United States Patent [19]

Maurer et al.

[11] Patent Number: 4,612,305
[45] Date of Patent: Sep. 16, 1986

[54] COMBATING PESTS WITH OXO-QUINAZOLINE-(THIONO)-PHOSPHORIC(PHOSPHONIC) ACID ESTERS AND ESTER-AMIDES

[75] Inventors: Fritz Maurer, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 636,520

[22] Filed: Aug. 1, 1984

Related U.S. Application Data

[63] Continuation-in-part of Ser. No. 398,254, Jul. 14, 1982, abandoned.

[30] Foreign Application Priority Data

Jul. 31, 1981 [DE] Fed. Rep. of Germany ....... 3130344

[51] Int. Cl.⁴ .................... A01N 57/16; A01N 57/32; A01N 57/24
[52] U.S. Cl. ........................ 514/80; 544/244; 544/287
[58] Field of Search ........................... 544/244; 514/80

[56] References Cited

U.S. PATENT DOCUMENTS

| 2,754,243 | 7/1956 | Gysin et al. | 514/80 |
| 3,894,020 | 7/1975 | Maurer et al. | 544/244 |
| 4,152,426 | 5/1979 | Maurer et al. | 514/80 |

FOREIGN PATENT DOCUMENTS

| 2223025 | 11/1973 | Fed. Rep. of Germany . | |
| 0000306 | 1/1969 | Japan | 544/244 |
| 0008508 | 4/1969 | Japan | 544/244 |
| 0025195 | 3/1981 | Japan | 544/244 |

OTHER PUBLICATIONS

Derwent Japanese, 1/9/69, vol. 8, No. 2, p. 1.
Derwent Japanese, 4/17/69, vol. 8, No. 16, p. 4.

*Primary Examiner*—Donald G. Daus
*Assistant Examiner*—Diana G. Rivers
*Attorney, Agent, or Firm*—Sprung, Horn, Kramer & Woods

[57] ABSTRACT

Oxo-quinazoline-(thiono)-phosphoric(phosphonic) acid esters and ester-amides of the general formula

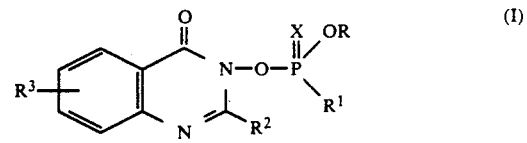

in which
R represents an optionally substituted alkyl radical,
$R^1$ denotes an optionally substituted alkyl, alkoxy, alkylthio, alkylamino, dialkylamino or aryl radical,
$R^2$ represents an optionally substituted alkoxy, alkylthio, alkylamino or dialkylamino radical and
$R^3$ represents a hydrogen or halogen atom and
X represents an oxygen or sulphur atom, which possess arthropodicidal activity.

6 Claims, No Drawings

COMBATING PESTS WITH OXO-QUINAZOLINE-(THIONO)-PHOSPHORIC(-PHOSPHONIC) ACID ESTERS AND ESTER-AMIDES

This is a continuation-in-part of application Ser. No. 398,254, filed July 14, 1982, now pending.

The invention relates to certain new oxo-quinazoline-(thiono)-phosphoric(phosphonic) acid esters and esteramides, to a process for their production and to their use as pest-combating agents, in particular as insecticides and acaricides.

It is known that certain oxo-quinazoline-thiono-phos-phosphoric acid esters, such as O,O-diethyl-O-3,4-dihydro-4-oxo-quinazolin-3-yl thionophosphoric acid esters and O,O-diethyl-O-3,4-dihydro-2-methyl-4-oxo-quinazolin-3-yl thionophosphoric acid esters can be used for combating pests (compare U.S. Pat. No. 3,894,020, issued July 8, 1975, and Japanese Patent Specification No. 8508/69). However, the insecticidal and acaricidal action of the known compounds is not always satisfactory, in particular at low concentrations of active compound and application rates.

The present invention now provides, as new compounds, the oxo-quinazoline-(thiono)-phosphoric(phosphonic) acid esters and ester-amides of the general formula

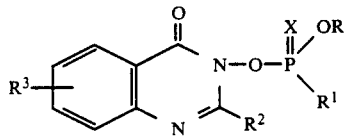

in which
R represents an optionally substituted alkyl radical,
$R^1$ represents an optionally substituted alkyl, alkoxy, alkylthio, alkylamino, dialkylamino or aryl radical,
$R^2$ represents an optionally substituted alkoxy, alkylthio, alkylamino or dialkylamino radical and
$R^3$ represents a hydrogen or halogen atom and
X represents an oxygen or sulphur atom.

According to the present invention we further provide a process for the production of a compound of the present invention, characterized in that a 3,4-dihydro-3-hydroxy-4-oxo-quinazoline of the general formula

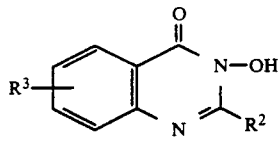

in which
$R^2$ and $R^3$ have the abovementioned meanings, is reacted with a (thiono)phosphoric(phosphonic) acid ester halide or ester-amide halide of the general formula

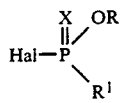

in which

R, $R^1$ and X have the abovementioned meaning and
Hal represents a halogen atom (preferably a chlorine atom),
if appropriate in the presence of an acid acceptor and, if appropriate, in the presence of a diluent.

The compounds of the present invention are distinguished by a high activity against animal pests, particularly by a high insecticidal and acaricidal activity.

Active compounds according to the present invention of the formula (I) surprisingly have a considerably higher insecticidal and acaricidal action than corresponding known compounds.

Preferred active compounds of the present invention are those in which
R represents an optionally substituted alkyl radical having 1 to 6 carbon atoms,
$R^1$ represents an optionally substituted alkyl, alkoxy, alkylthio, alkylamino or dialkylamino radical in each case having 1 to 6 carbon atoms per alkyl part, or a phenyl radical,
$R^2$ represents an optionally substituted alkoxy, alkylthio, alkylamino or dialkylamino radical having in each case 1 to 6 carbon atoms per alkyl part,
$R^3$ represents a hydrogen, fluorine, chlorine or bromine atom and
X represents an oxygen or sulphur atom.

Of these preferred compounds, those in which the radicals of R and $R^2$ are unsubstituted and $R^1$ represents alkyl, alkoxy, alkoxyalkoxy, alkylthio, alkylamino or dialkylamino in each case having 1 to 6 carbon atoms per alkyl part or phenyl, are particularly preferred.

Alkyl radicals of R and $R^1$, phenyl radicals of $R^1$ and also alkoxy, alkylthio and (di)alkylamino radicals of $R^1$ and $R^2$ can carry one or more, preferably 1 to 3, in particular 1 or 2, identical or different substituents. Examples which may be mentioned are halogen atoms (such as fluorine, chlorine and bromine atoms), cyano, and also alkoxy and alkylthio preferably having 1 to 5, in particular 1 to 3, carbon atoms.

The radicals R, $R^1$ and $R^2$ are preferably unsubstituted or the alkoxy radical $R^1$ is substituted by alkoxy, especially methoxy or ethoxy.

The alkyl radicals of R and $R^1$ and also the alkyl parts of the alkoxy radicals of $R^1$ and $R^2$ and of the alkylthio, alkylamino and dialkylamino radicals of $R^1$ and $R^2$ can be branched or unbranched and in each case contain 1 to 6, in particular 1 to 4, carbon atoms.

Very particular preferred compounds of the present invention are those, in which
R represents a methyl, ethyl, n-propyl, iso-propyl, n-butyl, iso-butyl or tert.-butyl radical,
$R^1$ and $R^2$ independently represent a methoxy, ethoxy, methoxymethoxy, methoxyethoxy, n-propoxy, iso-propoxy, n-butoxy, sec.-butoxy, iso-butoxy, tert.-butoxy, methylthio, ethylthio, n-propylthio, iso-propylthio, n-butylthio, iso-butylthio, sec.-butylthio, tert.-butylthio, (di)-methylamino, (di)-ethylamino, (di)-n-propylamino, (di)-iso-propylamino, (di)-n-butylamino, (di)-iso-butylamino, (di)-sec.-butylamino or (di)-tert.-butylamino radical, with $R^1$ additionally representing a methyl, ethyl, n-propyl, iso-propyl, n-butyl, iso-butyl, tert.-butyl or phenyl radical,
$R^3$ represents a hydrogen, chlorine or bromine atom, and
X represents an oxygen or sulphur atom.

If, for example, 7-chloro-3,4-dihydro-2-ethoxy-3-hydroxy-4-oxo-quinazoline and O-ethylethanephosphoric acid ester chloride are used as starting materials, the reaction according to the present invention is illustrated by the following reaction equation:

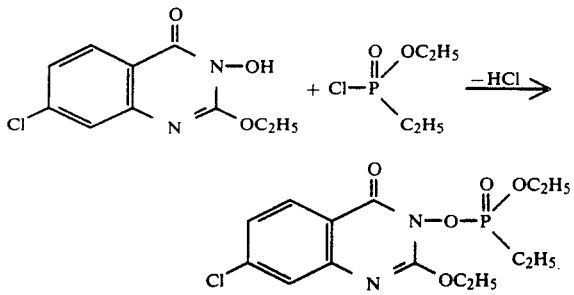

The 3,4-dihydro-3-hydroxy-4-oxo-quinazolines of formula (II) to be used as starting materials in the process according to the invention are novel and form a further subject of the present invention. Preferred compounds of formula (II) are those in which the radicals $R^2$ and $R^3$ have the meanings given above in the definition of the preferred, particularly preferred and very particularly preferred compounds of formula (I).

Examples of compounds of the formula (II) which may be mentioned ar 2-methoxy-, 2-ethoxy-, 2-n-propoxy-, 2-iso-propoxy, 2-n-butoxy, 2-sec.-butoxy, 2-iso-butoxy-, 2-tert.-butoxy-, 2-methylthio-, 2-ethylthio-, 2-n-propylthio-, 2-iso-propylthio-, 2-n-butylthio-, 2-sec.-butylthio-, 2-iso-butylthio-, 2-tert.-butylthio-, 2-(di)-methylamino-, 2-(di)-ethylamino-, 2-(di)-n-propylamino, 2-(di)-iso-propylamino-, 2-(di)-n-butylamino-, 2-(di)-iso-butylamino-, 2-(di)-sec.-butylamino-, 2-(di)-tert.-butylamino-3,4-dihydro-3-hydroxy-4-oxo-quinazoline and -7-chloro(bromo)-3,4-dihydro-3-hydroxy-4-oxo-quinazoline and -6-chloro(-bromo)-3,4-dihydro-3-hydroxy-4-oxo-quinazoline.

The novel compounds of the formula (I) may be prepared by generally customary methods, for example by reacting a 2-aminohydroxamic acid of the general formula

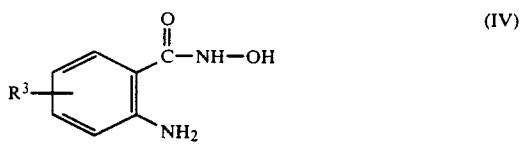

in which
R$^3$ has the abovementioned meaning, with an ortho-ester of the general formula $$R^2—C(OR^4)_3 \qquad (V)$$

in which
R$^2$ has the abovementioned meaning and
R$^4$ represents a methyl or ethyl radical,
if appropriate in the presence of a diluent (such as methanol) at a temperature between 20° and 160° C. (see U.S. Pat. No. 3,894,020, supra).

The O-aminohydroxamic acids of the formula (IV) required as starting materials are generally known compounds o organic chemistry. Examples which may be mentioned are: 2-amino-, 2-amino-4-chloro-, 2-amino-4-bromo-, 2-amino-5-chloro- and 2-amino-5-bromo-benzohydroxamic acid.

The ortho-esters of the formula (V) which are also required as starting materials are generally known compounds of organic chemistry. Examples which may be mentioned are: O-methyl-, O-ethyl-, O-n-propyl-, O-iso-propyl-, O-n-butyl-, O-iso-butyl-, O-sec.-butyl-, O-tert.-butyl-O,O,O-trimethyl-orthocarbonic acid esters and -O,O,O-triethyl-orthocarbonic acid esters; S-methyl-, S-ethyl-, S-n-propyl-, S-iso-propyl-, S-n-butyl-, S-iso-butyl-, S-sec.-butyl-, S-tert.-butyl-O,O,O-trimethylorthothiocarbonic acid esters and -O,O,O-triethyl-orthothiocarbonic acid esters; O,O,O,N-orthocarbonic acid tetramethyl ester-amide, O,O,O,N,N-orthocarbonic acid pentamethyl ester-amide; O,O,O-N-orthocarbonic acid tetraethyl ester-amide; O,O,O-N,N-orthocarbonic acid pentaethyl ester-amide; N-n-propyl-, N,N-di-n-propyl-, N-iso-propyl-, N,N-di-iso-propyl-, N,n-butyl-, N,N-di-n-butyl-, N-iso-butyl-, N,N-di-iso-butyl-, N-sec.-butyl-, N-tert.-butyl-O,O,O-trimethyl-orthocarbonic acid ester amide and -O,O,O-triethyl-orthocarbonic acid ester-amide.

Preferred (thiono)phosphoric(phosphonic) acid ester halides and ester-amide halides of formula (II) which are also used as starting materials for the process according to the invention for the production of active compounds of formula (I) are those in which the radicals R and R$^1$ have the meaning indicated in the definitions of the preferred, particularly preferred and very particularly preferred compounds of formula (I) and Hal represents a halogen atom, preferably a chlorine atom.

Examples which may be mentioned of compounds of the formula (III) are: O-methyl-, O-ethyl-, O-n-propyl-, O-iso-propyl-, O-n-butyl-, O-iso-butyl- and O-sec.-butyl(thiono)-methanephosphoric acid ester chloride: O-methyl-, O-ethyl-, O-n-propyl-, O-iso-propyl-, O-n-butyl-, O-isobutyl- and O-sec.-butyl-(thiono)-ethanephosphonic acid ester chloride; O-methyl-, O-ethyl-, O-n-propyl-, O-isopropyl-, O-n-butyl-, O-iso-butyl- and O-sec.-butyl-(thiono)propanephosphonic acid ester chloride; O-methyl-, O-ethyl-, O-n-propyl-, O-iso-propyl-, O-n-butyl-, O-iso-butyl- and O-sec.-butyl-(thiono)-butanephosphonic acid ester chloride; O,O-dimethyl-, O,O-diethyl-, O,O-di-n-propyl-, O,O-di-n-butyl-, O-methyl-O-ethyl-, O-methyl-O-n-propyl-, O-methyl-O-iso-propyl-, O-methyl-O-n-butyl-, O-methyl-O-iso-butyl-, O-ethyl-O-n-propyl-, O-ethyl-O-n-butyl-, O-ethyl-O-iso-butyl, O-n-propyl-O-n-butyl- and O-n-propyl-O-iso-butyl(thiono)-phosphoric acid diester chloride; O,S-dimethyl-, O,S-diethyl-, O,S-di-n-propyl-, O,S-di-iso-propyl-, O-methyl-S-ethyl-, O-methyl-S-n-propyl-, O-methyl-S-iso-propyl-, O-ethyl-S-methyl-, O-ethyl-S-n-propyl-, O-ethyl-S-iso-propyl-, O-n-propyl-S-methyl-, O-n-propyl-S-ethyl-, O-n-propyl-S-iso-propyl-, O-iso-propyl-S-methyl-, O-iso-propyl-S-ethyl- and O-iso-propyl-S-n-propyl-(thiono)-thiophosphoric acid diester chloride; O-methyl-N-(di)-methyl-, O-methyl-N-(di)-ethyl-, O-methyl-N-(di)-n-propyl-, O-methyl-N-(di)-iso-propyl-, O-ethyl-N-(di)-methyl-, O-ethyl-N-(di)-ethyl-, O-ethyl-N-(di)-n-propyl-, O-ethyl-N-(di)-iso-propyl-, O-n-propyl-N-(di)-methyl-, O-n-propyl-N-(di)-ethyl-, O-n-propyl-N-(di)-n-propyl, O-n-propyl-N-(di)-iso-propyl-, O-iso-propyl-N-(di)-methyl-, O-iso-propyl-N-(di)-ethyl-, O-iso-propyl-N-(di)-n-propyl(thiono)-phosphoric acid-amide ester chloride; O-methyl-, O-ethyl-, O-n-propyl-, O-iso-propyl-, O-n-butyl-, O-iso-butyl-, O-sec.-butyl-(thiono)-phenylphosphonic acid ester chloride.

Compounds of the formula (III) are known and can be prepared by generally customary known processes (see Methoden der organischen Chemie [Methods of Organic Chemistry] (Houben-Weyl-Müller, 4th edition, Volume 12/1 (1964), pages 607-618; Thieme-Verlag, Stuttgart).

The process according to the invention is preferably carried out with the use of a diluent. Possible diluents are virtually any of the inert organic solvents. Amongst these are in particular aliphatic and aromatic optionally halogenated, hydrocarbons (such as pentane, hexane, heptane, cyclohexane, petroleum ether, benzene, ligroin benzene, toluene, xylene, methylene chloride, ethylene chloride, chloroform, carbon tetrachloride, chlorobenzene and o-dichlorobenzene), ethers (such as diethyl ether, dibutyl ether, glycol dimethyl ether and diglycol dimethyl ether, tetrahydrofuran and dioxane), ketones (such as acetone, methyl ethyl ketone, methyl iso-propyl ketone and methyl isobutyl ketone), esters (such as acetic acid methyl ester and acetic acid ethyl ester), nitriles (such as acetonitrile and propionitrile), amides (such as dimethylformamide, dimethylacetamide and N-methyl-pyrrolidone), dimethyl sulphoxide, tetramethylene sulphone and hexamethylphosphoric acid triamide.

Any of the customary acid-binding agents can be used as acid acceptors. Alkali metal carbonates and alkali metal alcoholates (such as sodium carbonate, potassium carbonate, sodium methylate, potassium methylate, sodium ethylate and potassium ethylate) and also aliphatic, aromatic or heterocyclic amines (for example triethylamine, trimethylamine, dimethylaniline, dimethylbenzylamine and pyridine) have proved particularly suitable.

The reaction temperature can be varied within a wide range. The reaction is in general carried out at a temperature between 0° and 150° C., preferably between 10° and 100° C.

The process according to the invention is in general carried out under atmospheric pressure.

In carrying out the process according to the invention the starting materials are usually used in approximately equimolar amounts. A relatively large excess of either of the reactants does not yield any significant advantages. The reaction is in general carried out in a suitable diluent in the presence of an acid acceptor.

The compounds of the formula (I) are isolated in a customary manner. The melting point or the refractive index serve to characterize the compounds of the formula (I).

The active compounds are well tolerated by plants, have a favorable level of toxicity to warm-blooded animals, and are suitable for combating arthropod pests, especially insects and arachnidae, and nematodes, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficular auricularia;*

From the order of the Isoptera, for example Reticulitermes spp., from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophilia pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Phizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa;

from the order of the Siphonaptera, for example Xenopsylla cheopis and Ceratophyllus spp.;

from the class of the Arachnida, for example Scorpia maurus and Latrodectus mactans;

from the order of the Acarina, for example Acarus siro, Argas spp., Ornithodoros spp., Dermanyssus gallinae, Eriophyes ribis, Phyllocoptruta oleivora, Boophilis spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The plant-parasitic namatodes include Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp., and Trichodorus spp.

However the compounds are especially active against biting, as opposed to sucking, insects. Orders of biting insects which are especially attacked include Coleoptera such as Tenebrio molitor and Phaedon, Lepidoptera such as Plutella, and Diptera such as Phorbia.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperatures and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The present invention also provides pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids, or nematodes) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

PREPARATION EXAMPLES

EXAMPLE 1

(a) 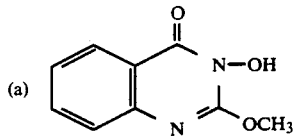 (IIa)

A mixture of 22.8 g (0.15 mol) of o-aminobenzohydroxamic acid, 50 ml of methanol and 27.2 g (0.2 mol) of orthocarbonic acid tetramethyl ester was boiled under reflux for 2 hours and was then cooled to 5° C. The product which had crystallized out was filtered off with suction. 17 g (60% of theory) of 2-methoxy-3-hydroxy-3,4-dihyro-4-oxo-quinazoline were obtained in the form of colorless crystals having a melting point of 220° C.

The following intermediates of the formula (II)

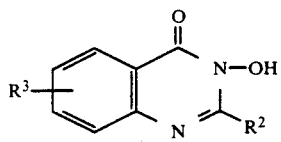 (II)

could be prepared analogously;

| Intermediate | $R^2$ | $R^3$ | Yield (% of theory) | Melting point (°C.) |
|---|---|---|---|---|
| b | $OC_2H_5$ | H | 86 | 154 |
| c | $OCH_3$ | 7-Cl | 44 | 206 |
| d | $n\text{-}OC_3H_7$ | | | |
| e | $iso\text{-}OC_3H_7$ | | | |
| f | $sec.\text{-}OC_4H_9$ | | | |

(b) 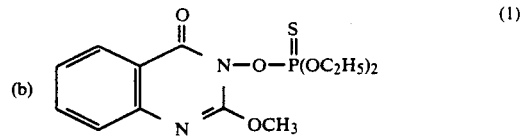 (1)

A mixture of 6.8 g (0.035 mol) of 3,4-dihydro-3-hydroxy-2-methoxy-4-oxo-quinazoline, 7.2 g (0.052 mol) of potassium carbonate, 6.6 g (0.035 mol) of O,O-diethylthionophosphoric acid diester chloride and 100 ml of acetonitrile was stirred for one hour at 45°–50° C. 200 ml of toluene were then added to it, the mixture was shaken twice with 200 ml of water in each case and the organic phase was dried over sodium sulphate. After distilling off the solvent, 9.2 g (76% of theory) of O,O-diethyl-O-3,4-dihydro-2-methoxy-4-oxo-quinazolin-3-yl-thionophosphoric acid ester were obtained in the form of colorless crystals having a melting point of 74° C.

The following compounds of the formula (I)

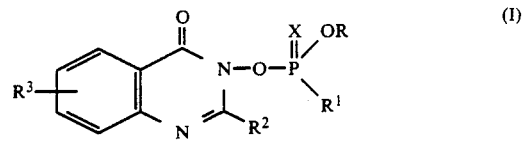 (I)

could be prepared analogously:

| Compound No. | R | $R^1$ | $R^2$ | $R^3$ | X | Yield (% of theory) | Refractive index; melting point (°C.) |
|---|---|---|---|---|---|---|---|
| 2 | $iso\text{-}C_3H_7$ | $CH_3$ | $OCH_3$ | H | S | 80 | 97 |
| 3 | $C_2H_5$ | $NH\text{—}iso\text{-}C_3H_7$ | $OCH_3$ | H | S | 80 | 108 |
| 4 | $C_2H_5$ | $OC_2H_5$ | $OC_2H_5$ | H | S | 77 | 67 |
| 5 | $C_2H_5$ | $OC_2H_5$ | $OCH_3$ | 7-Cl | S | 84 | 67 |
| 6 | $CH_3$ | $OCH_3$ | $OCH_3$ | H | S | | 69 |
| 7 | $C_2H_5$ | $SC_3H_7\text{—}n$ | $OCH_3$ | H | S | | $n_D^{22}$: 1.5773 |
| 8 | $C_2H_5$ | $SC_3H_7\text{—}n$ | $OCH_3$ | H | O | | |
| 9 | $C_2H_5$ |  | $OCH_3$ | H | S | | |
| 10 | $C_2H_5$ | $OC_2H_5$ | $OCH_3$ | H | O | | |
| 11 | $C_2H_5$ | $OC_2H_5$ | $n\text{-}OC_3H_7$ | H | S | | |
| 12 | $C_2H_5$ | $OC_2H_5$ | $iso\text{-}OC_3H_7$ | H | S | | |
| 13 | $CH_3$ | $OCH_3$ | $SCH_3$ | H | S | | |
| 14 | $CH_3$ | $OCH_3$ | $N(CH_3)_2$ | H | S | | |
| 15 | $C_2H_5$ | $OC_2H_5$ | $N(CH_3)_2$ | H | S | | |
| 16 | $C_2H_5$ | $OC_2H_5$ | $SCH_3$ | H | S | | |

-continued

| Compound No. | R | R¹ | R² | R³ | X | Yield (% of theory) | Refractive index; melting point (°C.) |
|---|---|---|---|---|---|---|---|
| 17 | $C_2H_5$ | $OC_2H_5$ | sec.-$OC_4H_9$ | H | S | | |
| 18 | $CH_3$ | $OCH_3$ | $SC_2H_5$ | $SC_2H_5$ H | S | | |
| 19 | $C_2H_5$ | $OC_2H_5$ | $SC_2H_5$ | H | S | | |
| 20 | $C_2H_5$ | $OC_2H_5$ | $SC_2H_5$ | H | S | | |
| 21 | $C_2H_5$ | $OC_2H_5$ | $N(C_2H_5)_2$ | H | S | | |
| 22 | —$CH_3$ | n-$OC_3H_7$ | —$OCH_3$ | H | S | 87 | $n_D^{19}$: 1.5525 |
| 23 | —$C_2H_5$ | n-$OC_3H_7$ | —$OCH_3$ | H | S | 91 | $n_D^{19}$: 1.5441 |
| 24 | —$C_3H_7$—n | n-$OC_3H_7$ | —$OCH_3$ | H | S | 87 | $n_D^{19}$: 1.5439 |
| 25 | —$C_2H_5$ | —$OCH_2CH_2$—$OCH_3$ | —$OCH_3$ | H | S | 87 | $n_D^{19}$: 1.5538 |
| 26 | —$C_2H_5$ | —$OC_4H_9$—n | —$OCH_3$ | H | S | | $n_D^{18}$: 1.5388 |

The pesticidal activity of the compounds of this invention is illustrated by the following biotest examples.

In these examples, the compounds according to the present invention are each identified by the number (given in brackets) of the corresponding preparative example.

The known comparison compounds are identified as follows:

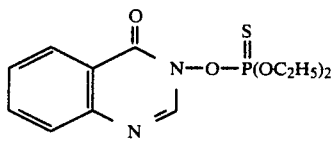

"Comparative compound A"

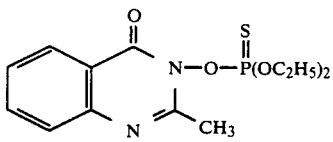

"Comparative compound B"

(Comparative compounds A and B are known from the state of the art mentioned at the beginning of the specification.)

EXAMPLE 2

Plutella test

Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (Brassica oleracea) were treated by being dipped into the preparation of active compound of the desired concentration and were infested with caterpillars of the diamond-back moth (Plutella maculipennis), as song as the leaves were still moist.

After the specified periods of time, the destruction in % was determined. 100% meant that all the caterpillars had been killed; 0% meant that none of the caterpillars had been killed.

In this test, the compounds (1), (4) and (5), for example at a concentration of 0.001%, after 3 days, showed a destruction of 90 to 100%, while the comparative compound A gave a destruction of 30%.

EXAMPLE 3

Myzus test

Solvent: 3 parts by weight of acetone
Emulsifier: 1 part by weight of alkylaryl polyglycol ether To produce a suitable preparation of active compound, 1 part by weight of active compound was mixed with the tested amount of solvent and the stated amount of emulsifier, and the concentrate was diluted with water to the desired concentration.

Cabbage leaves (Brassica oleracea) which had been heavily infested with peach aphids (Myzus persicae) were treated by being dipped into the preparation of active compound of the desired concentration.

After the specified periods of time, the destruction in % was determined. 100% meant that all the aphids had been killed; 0% meant that none of the aphids had been killed.

In this test, the compounds (1), (2), (4) and (5), for example at a concentration of 0.1%, after 1 day, showed a destruction of 95 to 100%, while the comparative compound B gave a destruction of 60%.

EXAMPLE D

Tetranychus test (resistant)

Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (Phaseolus vulgaris) which were heavily infested with the common spider mite or two-spotted spider mite (Tetranychus urticae) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, the compounds (1) and (2), for example at an active compound concentration of 0.1%, after 2 days, showed a destruction of 70 to 90%, while the comparative compound B gave no destruction (0%).

EXAMPLE 5

Critical concentration test/soil insects

Test insect: Phorbia antiqua maggots in the soil
Solvent: 3 parts by weight of acetone Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

In this test, the compounds (1), (3) and (4), for example at a concentration of 10 ppm, showed a destruction of 100%, while comparative compound B gave no destruction (0%).

EXAMPLE 6

Critical concentration test/soil insects

Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

In this test, the compounds (1), (2), (4) and (5), for example at a concentration of 20 ppm, showed a destruction of 100%, while the comparative compounds A and B gave no destruction (0%).

It will be appreciated that the instant specification and examples are set forth by way of illustration and not limitation, and that various modifications and changes may be made without departing from the spirit and scope of the present invention.

In the claims:

1. A method of combating pests selected from the group consisting of Phaedon, Plutella, Phorbia and Tenebrio, comprising applying to the pests, or to a habitat thereof, a pesticidally effective amount of an oxoquinazoline-(thiono)-phosphoric(phosphonic) acid ester or ester-amide of the formula

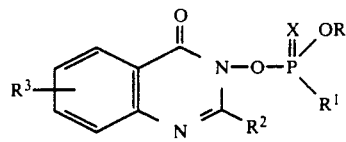

R is an alkyl radical having 1 to 6 carbon atoms,
$R^1$ is an alkyl, alkoxy, alkoxyalkoxy, alkylthio, alkylamino or dialkylamino radical in each case having 1 to 6 carbon atoms per alkyl moiety or a phenyl radical,
$R^2$ is a alkoxy, alkylthio, alkylamino or dialkylamino radical in each case having 1 to 6 carbon atoms per alkyl moiety,
$R^3$ is a hydrogen, fluorine, chlorine or bromine atom, and
X is an oxygen or sulphur atom.

2. A method according to claim 1, wherein such compound is O,O-diethyl-O-3,4-dihydro-2-methoxy-4-oxo-quinazolin-3-yl-thiono-phosphoric acid ester of the formula

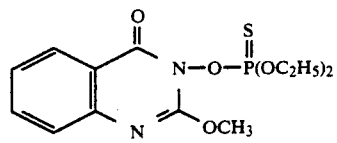

3. A method according to claim 1, wherein such compound is O-isopropyl-O-3,4-dihydro-2-methoxy-4-oxo-quinazolin-3-yl-methanethionophosphonic acid ester of the formula

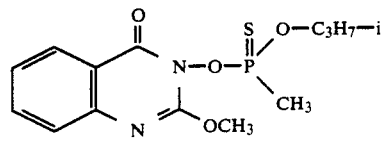

4. A method according to claim 1, wherein such compound is O,O-diethyl-O-3,4-dihydro-2-ethoxy-4-oxo-quinazolin-3-yl-thino-phosphoric acid ester of the formula

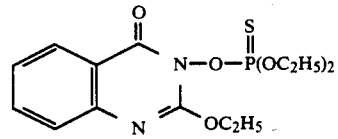

5. A method according to claim 1, wherein such compound is O,O-dimethyl-O-3,4-dihydro-2-methoxy-4-oxo-quinazolin-3-yl-thiono-phosphoric acid ester of the formula

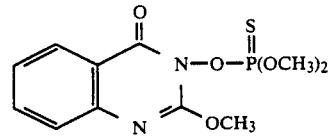

6. A method according to claim 1, wherein such compound is O-ethyl-S-n-propyl-O-3,4-dihydro-2- methoxy-4-oxo-quinazolin-3-yl-thiono-phosphoric acid ester of the formula
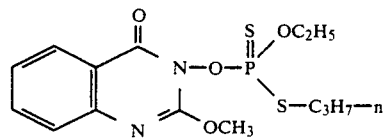
* * * * *